United States Patent [19]

Harvey

[11] 4,260,781

[45] Apr. 7, 1981

[54] PROCESS FOR THE MANUFACTURE OF CARBAMATES

[75] Inventor: Robert J. Harvey, Teaneck, N.J.

[73] Assignee: Halcon Research and Development Corp., New York, N.Y.

[21] Appl. No.: 42,675

[22] Filed: May 25, 1979

[51] Int. Cl.³ ................. C07C 125/063; C07C 125/07
[52] U.S. Cl. ..................................... 560/24; 260/464;
  252/441; 252/449; 260/465 D; 252/472;
  260/465.4; 560/9; 560/25; 560/26; 560/27;
  560/30; 560/31; 560/32; 560/33; 560/115;
  560/132; 560/133; 560/135; 560/136; 560/137;
  560/148; 560/157; 560/158; 560/159; 560/160;
  560/161; 560/162; 560/163; 560/164; 560/165;
  560/29; 252/438; 252/439; 252/440
[58] Field of Search ............... 560/9, 25, 24, 30, 31,
  560/26, 32, 33, 29, 115, 132, 133, 135, 27, 136,
  137, 148, 157, 158, 159, 160, 161, 162, 163, 164,
  165; 260/464, 465 D, 465.4

[56] References Cited

U.S. PATENT DOCUMENTS

| | | | |
|---|---|---|---|
| 3,099,689 | 7/1963 | Cragg | 260/561 |
| 3,338,956 | 8/1967 | Morentfield | 560/24 |
| 3,384,655 | 5/1968 | Anderson et al. | 560/24 |
| 3,448,140 | 6/1969 | Gamlen et al. | 560/24 |
| 3,454,620 | 7/1969 | Gamlen et al. | 560/24 |
| 3,467,694 | 9/1969 | Hardy et al. | 560/25 |
| 3,531,512 | 9/1970 | Hardy et al. | 560/25 |
| 3,629,311 | 12/1971 | Anderson et al. | 260/455 B |
| 3,895,054 | 7/1975 | Zajacek et al. | 560/25 |
| 3,956,360 | 5/1976 | Zajacek et al. | 560/24 |
| 3,993,685 | 11/1976 | Zajacek et al. | 560/24 |
| 4,052,437 | 10/1977 | Licke | 560/24 |
| 4,080,365 | 3/1978 | Hirai et al. | 560/24 |
| 4,100,351 | 7/1978 | Romano et al. | 560/25 |
| 4,134,880 | 1/1979 | Miyata et al. | 560/25 |
| 4,170,708 | 10/1979 | Hirai et al. | 560/24 |
| 4,178,455 | 12/1979 | Hirai et al. | 560/24 |
| 4,186,269 | 1/1980 | Hirai et al. | 560/25 |

FOREIGN PATENT DOCUMENTS 634690 1/1962 Canada .
1486399 9/1977 United Kingdom .

OTHER PUBLICATIONS

Balling, et al., "Chem. Absts.," 73, 66302(p), 1970.
Franz et al., *J. Org. Chem.*, 26, 3309 (1961).
Baiocchi, et al., *J. Org. Chem.*, 21, 1546 (1956).
Miyata et al., European Patent Application 815, published 2/21/79.

*Primary Examiner*—Natalie Trousof
*Assistant Examiner*—G. T. Breitenstein
*Attorney, Agent, or Firm*—William C. Long; David Dick; Jack B. Murray, Jr.

[57] ABSTRACT

A process for the production of carbamates is provided in which an organic primary or secondary amine is contacted, in the substantial absence of reactive oxygen, with a source of carbon monoxide, an organic compound containing at least one hydroxyl group, and a metal reactant comprising at least one member selected from the group consisting of compounds and complexes of Group VIII of the Periodic Table.

14 Claims, No Drawings

PROCESS FOR THE MANUFACTURE OF CARBAMATES

CROSS-REFERENCE TO RELATED APPLICATION

This application is related to co-pending applications of D. Moy, Ser. No. 7,104, filed Jan. 29, 1979; Ser. No. 7,105, filed Jan. 29, 1979; application, Ser. No. 42,676, filed May 9, 1979, filed on even date herewith.

BACKGROUND OF THE INVENTION

1. Field of the Invention

This invention relates to the preparation of carbamates, and more specifically to the preparation of carbamates by the direct carbonylation of primary and secondary amines.

2. Description of the Prior Art

Carbamates, which are also referred to herein as "urethanes", are industrial chemicals of enormous significance, and much research has been performed in search of economical processes for their manufacture. One such process involves the formation of a primary amine such as aniline from the corresponding organic nitro compound (e.g., nitrobenzene) and reaction of the resulting primary amine with phosgene to form a carbamyl chloride salt which is then thermally decomposed to the corresponding isocyanate. Recovery and reaction of the isocyanate with an alcohol yields the carbamate. Due to the high toxicity of phosgene, and to the corrosive nature of systems in which the chloride ion is employed, alternative processes have been sought which would remove these disadvantages.

U.S. Pat. No. 3,467,687 relates to the preparation of organic isocyanates by reacting an aromatic nitroso compound with CO in the presence of catalyst and a Lewis acid under anhydrous, hydrogen-free conditions. U.S. Pat. No. 3,641,092 reacts a primary amine with CO and palladium chloride to form isocyanates. U.S. Pat. No. 3,405,156 forms isocyanates from saturated aliphatic primary amines or aromatically unsaturated primary amines by reaction of the amine with CO and a platinum group metal salt. See also E. W. Stern, et al., 31 *J. Org. Chem.* 596 (1965). U.S. Pat. No. 3,070,618 relates to the production of polyisocyanates from polyamines and CO by reaction with a metal carbonyl (or suitable mixtures of CO and oxygen) under catalytic conditions.

U.S. Pat. No. 3,644,462 produced isocyanates by carbonylation of organic nitro compounds employing a catalyst system comprised of a noble metal halide and certain primary, secondary and tertiary amines. However, the selectivity to the isocyanate was comparatively low and the required recovery and conversion of the isocyanate to a urethane product would be expected to reduce selectivities to the urethane still further.

Accordingly, a large number of processes were developed to carbonylate an organic nitro compound with carbon monoxide in the presence of an organic hydroxy compound and certain catalyst systems to obtain the corresponding urethane. Exemplary references to these processes and their catalyst systems are as follows: (1) U.S. Pat. Nos. 3,338,956 (carbonyls of metals of Groups VI-B, VII-B and VIII); 3,448,140 (complex compound of a transition metal having atomic number of 21 to 29, 39 to 47 and 71 to 79, inclusive, containing ligands of P, As, or Sb); 3,467,694 (noble metal and a Lewis acid); 3,531,512 (palladium and a Lewis acid); 3,895,054 (Se, S or Te); 3,956,360 secondary or tertiary amine); 3,895,054 (Se, S or Te); 3,956,360 (Se, S or Te); 3,993,685 (tertiary amine and a platinum group metal or compound thereof); 4,052,437 (rhodium oxide); and 4,080,365 (Se+base+aromatic amino or urea promoter); (2) British Pat. Nos. 1,089,132 (metal carbonyls of Groups VI-B, VII-B and VIII and multivalent metals or their salts); 1,469,222 (palladium group metal halide and a nitrogen-containing heterocyclic compound); and 1,485,108 (Se); and (3) French Pat. of Addition No. 2,008,365, as cited in 73 *Chem. Abs.* 66302p (1970) (palladium, $Al_2O_3$ or $Fe_2O_3$).

Urethanes have also been formed by reacting an alcohol with urea. See, e.g., P. Adams, et al., *Chem. Rev.*, vol. 65, 567, 596–572 (1965.)

While the above processes allow direct formation of carbamates from nitro- and urea-compounds, a one-step process for converting amines to carbamates would also be helpful. However, it was long believed that carbonylation of such amines only yields ureas or formamides. Thus, Hagelloch, *Ber.*, vol. 83, 258 (1950) reacted aniline and COS in ethanol to form low yields (1–3%) of 1,3-diphenyl urea, and German Pat. No. 863,800 (1953) converted aniline to high yields of urea and/or N-substituted formamides with CO in the presence of nickel iodide, powder nickel or cobalt (activated with MgO or $SiO_2$) as catalyst.

U.S. Pat. No. 3,099,689 obtained formamides by reaction of aniline with CO in the presence of organometallic compounds of metals of Groups IVB, VB, VIB, VIIB or VIII of the Periodic Table.

U.S. Pat. No. 4,052,454 formed unsymmetrical ureas by the reaction of nitrogenous organic compounds with aniline, carbon monoxide and sulfur or selenium and certain bases, and British Pat. No. 1,275,702 produced ureas from primary or secondary mono- or diamines by reaction with CO in the presence of Se. N. Sonoda et al., *J. Amer. Chem. Soc.*, vol. 92 (23), p. 6344 (1971) obtained very high yields of urea from ammonia or aliphatic amines, CO and $O_2$ in the presence of Se, and K. Kondo et al., *J. Chem. Soc. Chem. Comm.*, 307 (1972) obtained stoichiometric yields of urea by carbonylation of aromatic amines with CO, $O_2$ and Se, employing a strongly basic tertiary amine, such as triethyl amine, as co-catalyst.

R. A. Franz et al., 26 *J. Org. Chem.* 3309 (1961) found that tertiary aliphatic amines, KOH and CaO or MgO in methanol were urea catalysts in the reaction of aromatic amines with CO and S. U.S. Pat. No. 2,877,268 disclosed obtention of "excellent yields" of urea by use of alkaline catalysts with a dissociation constant of greater than $1 \times 10^{-10}$: tertiary alkyl amines of 1 to 18 carbon atoms, quaternary ammonium hydroxides, alkaline earth metal and alkali metal hydroxides, alkaline and alkali metal salts (such as sodium oleate), MgO (in methanol), Ca (in methanol) and certain substituted aryl and aralkyl amines. Similarly, diuredides were obtained in Canadian Pat. No. 634,690 by reacting aromatic diamines with CO,S and certain aliphatic or aromatic secondary amines in methanol.

Thio-derivatives of amines have also been produced by carbonylations. U.S. Pat. No. 3,636,104 formed N,N'-diaryl thioureas by reacting aniline with $CS_2$ in pyridine or alcohol with the addition of S or $H_2O$. Alkylamine salts of N-alkyl thiocarbamic acid were prepared in U.S. Pat. No. 2,655,534 by reacting COS and a primary or secondary aliphatic amine. U.S. Pat. Nos.

3,392,197 and 3,539,587 prepared substituted thioureas and monothiocarbamates from primary and secondary amines employing CO and sulfur or sulfur compounds. Thiocarbamates have also been prepared by reaction of amines and disulfides in equimolecular ratio with carbon monoxide in the presence of selenium catalysts and triethylamine. See. P. Koch, *Tetrahedron Letters* No. 25, pp. 2087–2088 (1975); West German Patent Publication No. 2,617,917 as cited in 86 *Chem. Abs.* 43426 m (1977).

In attempting to carbonylate amines to a carbamate product. F. Baiocchi, et al., 21 *J. Org. Chem.* 1546 (1956) prepared methyl-N-phenyl carbamate by reacting aniline and COS in methanol employing either zinc peroxide, di-tert-butyl peroxide or $O_2$ to induce the reaction. Magnesium peroxide was found to be not operative, and other peroxides ($H_2O_2$ in $H_2O$ and cumene hydroperoxide in methanol, with and without sodium methoxide), yielded very large amounts of 1,3-diphenyl urea. Netherlands Pat. No. 94,613 converted aliphatic primary and secondary amines to urethanes by reaction with CO in the presence of alcohols and stoichiometric amounts of certain cupric compounds. R. A. Franz et al., 28 *J. Org. Chem.* 585 (1963) obtained urethanes from aniline COS and methanol in the presence of triethyl amine. Certain metal acetates ($Hg^{+2}$, $Tl^{+3}$ and $Cu^{+2}$) were used in T. Saegusa, et al., *Tetrahedron Letters* No. 42, pp. 4123–4126 (1967) in a stoichiometric reaction with piperidine, CO and $CH_3OH$ to form urethanes. Use of the metal acetates of $Ag^{+1}$, $Cd^{+2}$ and $Zn^{+2}$ gave only trace carbmate product, even after 98 hours of reaction.

Higher urethane yields have been provided by U.S. Pat. Nos. 3,384,655 (issued in 1968 to Anderson et al.) and 3,629,311 (issued in 1971 to Anderson et al.) and K. Kondo, et al., *Chem. Letters*, pp. 373–374 (Chem. Soc. Japan 1972). In the Anderson et al. process, a secondary (or a mixture of secondary and tertiary) amine is first reacted with COS and an alcohol to form an adduct containing the urea, COS and alcohol, followed by a low temperature oxidation of the adduct with $O_2$, optionally in the presence of soluble Fe, Ni, Co, Cu, Hg, Pd, Pt or Au halide, sulfate or nitrate promoters, to form the desired urethane, elemental sulfur and water. Kondo et al. reacted a primary amine, CO, Se and methanol in the presence of triethylamine, followed by oxidation with $O_2$ of the foregoing mixtures, to yield the urethane, and to form a Se precipitate and water. However, the required use of $O_2$ (or peroxides as in the Baiocchi process) is industrially severely disadvantageous due to the ease with which aniline is oxidized to a wide variety of by-products and due to the obvious explosive hazards associated with mixtures of oxygen, carbon monoxide and alcohol. The explosive hazards require careful attention to temperature controls and use of expensive processing equipment. A further disadvantage to the use of oxygen is the by-product water which is formed and which then reacts with the carbamate to ultimately form a urea. To avoid the urea problem, water absorbing agents must be added and additional care must be taken to use anhydrous reactants to avoid further urea being formed. Both of these precautions require added processing expense.

U.S. Pat. Nos. 3,445,497, 3,502,706 and 3,632,624 relate to the formation of an adduct by reaction of tertiary amines, alcohols and carbon dioxide in the presence of certain metallic salts. These adducts are then further reacted to form such products as metal alkyl carbonates and thiolcarbonates.

European Patent Publication No. 815 (Mitsui Toatsu Chemicals, published Feb. 21, 1979) (which is not believed by applicant to comprise prior art) relates to the preparation of N-aryl or N-aralkyl substituted urethanes in which an aryl or aralkyl primary amino compound having a nitro, nitroso or carbamate group, is reacted with an organic hydroxyl-group containing compound and CO in the presence of a catalyst comprising a Pd, Rh or Ru metal compound and a Lewis acid compound promoter, preferably in the presence of from 1 to 70 moles of water per mole of the aryl or aralkyl primary amino compound. However, this process is not readily adaptable to producing carbamates using non-catalytic systems, and the Mitsui Toatsu applicants were unable to obtain detectable carbamate employing aryl or aralkyl primary amines which were not so substituted.

SUMMARY OF THE INVENTION

According to the process of the present invention, carbamates are produced by contacting an organic primary or secondary amine, in the substantial absence of reactive oxygen, with a source of carbon monoxide, an organic compound containing at least one hydroxyl group and a metal reactant comprising at least one member selected from the group consisting of compounds and complexes of metals of Group VIII of the Periodic Table.

The process of the present invention can achieve surprisingly high selectivities to the carbamate, with selectivities of up to about 85% (based on metal reactant reacted) and more being observed. Thus, the process produces only limited amounts of ureas, formamides and other by-products. Moreover, the present invention does not require the use of molecular $O_2$ or a peroxidic reactant to effect the formation of the carbamate product, minimizing the safety hazards and urea-formation problems attending the use of such reactants. Further, the amine reactants of this invention are not required to be first substituted by a $NO_2$, NO or carbamate group as in European Patent Application No. 815, cited above.

DETAILED DESCRIPTION OF THE INVENTION

Any organic primary or secondary amine capable of being converted to an organic carbamate may be employed as a reactant. Aliphatic amines, alicyclic amines and aromatic amines are operable. These amines include primary amines of the formula $RNH_2$ wherein R is alkyl, aryl, alkaryl, aralkyl, and cycloalkyl, and secondary amines of the formula $RNH(R')$ wherein R and R' are independently selected from the group consisting of alkyl, aryl, alkaryl, aralkyl and cycloalkyl. Also included as operable organic amines are primary and secondary amines containing fused rings and heterocyclic substituents. The primary and secondary amines may be substituted or unsubstituted, and when substituted preferably contain inert substituents such as alkyl, aryl, alkaryl, aralkyl, cycloalkyl, halogen (Cl, Br, F and I) cyano, tertiary amino, carboxyl, esters, ethers and thioether groups. Preferably, the amine reactant contains no substitution by OH—, <C═O (i.e., ketonic or aldehydic) or sulfonic acid groups since such groups interfere with the desired carbonylation reaction to the selected carbamates. The foregoing suitable hydrocarbon substituents to the R and R' groups can themselves be substituted by one or more amino groups. Exemplary of such amino substituted hydrocarbyl substituents to the R and R' groups are amino-substituted aralkyls (e.g.,

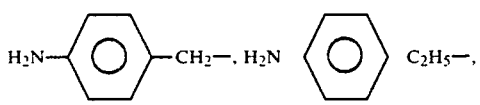

and the like), amino-substituted alkyl (e.g., $H_2NCH(CH_3)$—, $H_2NC_2H_5$—and the like) and amino-substituted alkaryls (e.g.,

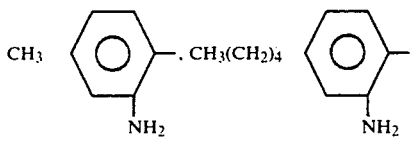

and the like).

Also included as reactants in this invention are amines of the formula $R(NH_2)_m$ wherein R is as defined above and wherein m is an integer of from 2 to 5, preferably of from 2 to 3. Thus, aliphatic, alicyclic and aromatic diamines, such as ethylenediamine, hexamethylenediamine and other homologues and isomers of 2 to 10 carbon atoms are operable. The aromatic diamines include phenylenediamine, toluenediamine and naphthylenediamine. Phenylenetriamine also is operable. Polymeric amines having repeating polymer units based on any of the above amines can also be used (e.g., polymeric methylene dianiline).

Examples of R and R' substituents of the amines of each of the above formulas are alkyl radicals derived from straight and branched-chained alkanes of from 1 to 20, preferably from 1 to 12, carbon atoms (such as methyl, ethyl, isopropyl, butyl decyl, dodecyl, isostearyl, and the like); aryl of 6 to 18, preferably 6 to 12, carbon atoms (such as phenyl, naphthyl, anthryl and the like), alkaryl and aralkyl of 7 to 24, preferably 7 to 12, carbon atoms (such as benzyl, tolyl, p-butyl phenyl, dihexylphenyl; isostearyl phenyl, and the like) and cycloalkyl of 3 to 12 carbon atoms (such as cyclohexyl, cyclopentyl, cyclobutyl, cyclododecyl and the like).

Typical examples of suitable amines which can be reacted to form carbamates include the following primary amines such as aniline, tolyl amines, xylyl amines, naphthyl amines, anthryl amines, benzyl amine, 1- or 2-bromoethyl benzyl amine, cyclohexylamine, bis-aminoaryl-substituted alkylenes (e.g., compounds of the formula

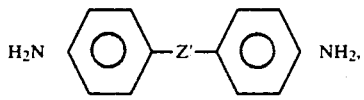

wherein Z' is alkylene of 1 to 6 carbon atoms, such as methylene, ethylene, trimethylene, tetramethylene and the like), the diamino toluenes and the like.

Especially preferred as amines in the process of this invention are primary amines of up to 14 carbon atoms. Most preferred are aromatic primary mono- and diamines of from 6 to 13 carbon atoms. Examples of most preferred monoamines are aniline, and of most preferred diamines are 2,4-diamino-toluene and 4,4'-methylene dianiline.

The source of the carbon monoxide employed as reactant in this invention is not critical and thus carbon monoxide can be employed, in any form (e.g., as a gas), as a pure material, or in admixtures with other materials which do not adversely affect the desired reaction. For example, carbon monoxide gas can be employed in admixture with materials normally found in synthesis gas (generally containing from about 50 to 80 volume % CO), such as hydrogen, $CO_2$ and the like. Of course, inert gases such as $N_2$, Ar and the like can be present. The carbon monoxide can also be introduced to the reaction zone in a chemically combined form with one or more of the desired components of the catalyst system. For example, the carbon monoxide can be chemically combined as a metal carbonyl, which under the conditions of the reaction will release carbon monoxide for reaction in the process with the desired amine. Such metal carbonyls are known materials. Thus, as used herein, the term "source of carbon monoxide" is intended to refer to CO or a chemically combined or complexed form thereof which releases CO under the conditions of the reaction. The preferred source of carbon monoxide is CO.

The reaction is preferably conducted in the substantial absence of "reactive oxygen", that is, the amount of molecular oxygen, and organic and inorganic peroxides in the reaction zone, whether dissolved, suspended, or in the gaseous state, should be less than 1 weight percent, and preferably less than about 0.1 weight percent, of amine reactant changed to the reaction zone.

Organic compounds containing at least one hydroxyl group suitable for use in the process in the present invention include mono- or polyhydric alcohols containing primary, secondary or tertiary hydroxyl groups and mixtures thereof. The alcohols can be aliphatic or aromatic and can bear other substituents in addition to hydroxyl groups, but the substituents should, except as hereinafter defined, preferably be non-reactive with carbon monoxide under the process conditions.

Generally, the hydroxyl group-containing compounds comprise compounds of the formula $Z(OH)_n$ wherein n is 1 or more and preferably from 1 to 3, and Z is an optionally substituted aryl, aliphatic, cycloaliphatic or araliphatic group, preferably containing from 1 to 20 carbon atoms, more preferably from 1 to 7 carbon atoms. The group Z can therefore be alkyl, cycloalkyl, alkylene, cycloalkylene, aryl, or aralkyl, which groups can be substituted by alkyl, alkoxy, aryl or aryloxy groups normally containing up to 7 carbon atoms, and derivatives of the foregoing in which one or more carbon atoms are substituted by oxygen, nitrogen or sulfur atoms. The foregoing groups can also be substituted by sulfoxide, sulfone, tertiary amine, amide or carboxylic ester groups.

Exemplary hydroxyl group-containing compounds are monohydric alcohols such as methanol, ethanol, n-propanol, sec-propanol, n-iso- and tert-butanol, amyl alcohol, hexyl alcohol, lauryl alcohol, cetyl alcohol, benzyl alcohol, chlorobenzyl alcohol, methoxy benzyl alcohol, methoxy ethanol, butoxy ethanol, cyclohexyl alcohol, phenol and the like. Exemplary polyhydric compounds include diols such as ethylene glycol, diethylene glycol, propylene glycol and dipropylene glycol, triols such as glycerol, trimethylolpropane, hexanetriol, tetrols such as pentaerythritol and the like. Ethers of the foregoing polyols can also be employed provided that at least one OH group remains unetherified. The etherifying group in such ether alcohols normally will contain up to 4 carbon atoms and are preferably selected from the group consisting of alkyl, cycloalkyl or aralkyl groups which can themselves be substituted.

Especially suitable hydroxy-containing compounds are the lower mono- and polyhydric alkanols. Exemplary of such especially suitable compounds are methanol, ethanol, p-propanol, isopropanol, butanol, sec-butanol, isobutanol, ethylene glycol, glycerol and trimethylol propane.

The metal reactants which are suitable for use in the process of this invention comprise members selected from the group consisting of compounds and complexes of metals of Group VIII of the Periodic Table, wherein the metal is at least a divalent state, i.e., the metal is in a +2 valence state or higher. Therefore, useful in this invention are compounds and complexes of Fe, Ru, Os, Co, Rh, Ir, Ni, Pd and Pt. The compound or complex containing any of the foregoing metals can be inorganic or organic, and mixed salts of the above metals can also be used. Exemplary of suitable inorganic salts are the oxides, hydroxides, sulfides, silicates, sulfates, phosphates, arsenates, nitrates, carbonates, halides (e.g., fluorides, chlorides, bromides, iodides), and the like.

Illustrative of inorganic Group VIII metal salts which can be employed are $PdCl_2$, $PtBr_2$, $Ru_2(SO_4)_3$, $Rh(NO_3)_3$, $OsO_4$, $IrF_3$, $Fe_2S_3$, $CoI_2$, $Ni_3(PO_4)_2$, and the like. Especially preferred Group VIII metal compounds are Pd and Co compounds, of which $PdCl_2$, $PdBr_2$, $CoI_2$, $CoCl_2$, $Pd(NO_3)_2$, $CoSO_4$, $PdI_4$ and $CoBr_2$ are exemplary.

A wide variety of organic solvents can also be employed in the reaction zone. Suitable organic solvents include alkanes such as cyclohexane, hexane, octane and the like; aromatic solvents such as benzene, toluene, xylene; nitrile solvents such as acetonitrile and benzonitrile; amide type solvents such as N, N-dimethyl formamide and N, N'-dimethyl acetamide; aliphatic, alicyclic or aromatic sulfoxide and sulfone solvents, such as dimethyl sulfoxide; aliphatic halogenated hydrocarbons such as 1, 1,2-trichloro-1, 2, 2-trifluoroethane; halogenated aromatic hydrocarbons such as monochlorobenzene, dichlorobenzene and trichlorobenzene; esters; and ether solvents such as tetrahydrofuran, 1,4-dioxane, 1,2-dimethoxyethane and the like. The ether compounds, for example can be aliphatic, aromatic or heterocyclic, and they can also be either mono or polyethers, or combinations of these compounds. When the hydroxy-containing organic compound is a liquid under reaction conditions, it sometimes can function as a solvent and is generally preferred. The solvent can also comprise an organic base as tertiary amines, heterocyclic compounds and mixtures thereof. Exemplary of suitable tertiary amines are those having the general formula LNL'(L''), wherein L, L' and L'' are independently selected from the group consisting of alkyl of 1 to 20 carbon atoms, aryl of 6 to 18 carbon atoms, alkaryl and aralkyl of 7 to 20 carbon atoms and cycloalkyl of from 3 to 12 carbon atoms. Preferred are the tertiary amines wherein L, L' and L'' are each alkyl of from 1 to 4 carbon atoms. Suitable illustrative tertiary amines are tri-n-propyl amine, tri-ethyl amine, dimethylethyl amine, dimethylpropyl amine, dimethylbenzyl amine, and the like. Suitable heterocyclic compounds include those containing at least one nitrogen atom in the cyclic moiety. Exemplary of such nitrogen-containing basically reacting compounds are pyridine, pyridazine, pyrimidine, pyrazine, piperazine, triazines, tetrazines, pyrrole, isopyrrole, pyrazole, imidazole, quinolines, and the like. Especially preferred nitrogen-containing compounds are pyridine and the dialkylamino pyridines.

At higher temperatures and pressures the process of the invention can advantageously be carried out in an inert diluent. The preferred inert diluents are those in which the non-gaseous reactants are soluble, including some of the solvents mentioned above. Suitable inert diluents include aliphatic or aromatic hydrocarbons such as n-pentane or toluene, ethers, and esters.

Water is detrimental to carbamate yields employing the process of this invention, and, therefore, it is preferred to employ substantially anhydrous reaction conditions and to employ as reactants those that are substantially anhydrous, although minor amounts of water introduced, for example, as water of hydration in any of the metal reactants, can be introduced without marked effect on product yield or quality. In general, the amount of water in the reaction zone should be limited to a concentration of less than about 1 weight percent, based on the amine reactant charged to the reaction zone. To effect such desired low levels of water, a water absorbing agent can also be employed in the reaction zone. Suitable water absorbing agents are described in U.S. Pat. Nos. 3,384,655 and 3,629,311. The need for such water absorbing agents is further reduced by the fact that water is not a by-product of the reaction to the desired carbamate using the process of the present invention. As used herein, the term "in the substantial absence of water" is intended to refer to water concentrations of less than about 1 weight percent, based on the amine reactant charged to the reaction zone.

The invention is preferably carried out with at least equal molar amounts of the hydroxyl-containing compound, carbon monoxide and the amine reactant being present. Preferably, however, a molar excess of the hydroxy-congaining compound is present.

The metal reactants of this invention will be generally used in an amount sufficient to provide at least one mole of the reactant metal (calculated as the metal) for each mole of amine reactant charged. While the metal compounds can be used in larger amounts, use of greater than about 5 moles of metal compound (calculated as the metal) per mole of amine reactant charged will generally be uneconomical. Of course, less than an equal molar amount of the reactant metal can be used, although this will necessarily limit the amount of amine reactant which will be converted during the reaction. Thus, use of metal reactant in an amount less than that which would provide a metal reactant: amine reactant molar ratio of 0.05:1 will generally also be uneconomical. Typically, therefore, the metal reactant to amine reactant molar ratio will range from about 0.05:1 to 5:1 and preferably from about 0.1:1 to 1:1. With respect to the term "amine reactant", reference is to the active nitrogen containing group, e.g., the amine group. Thus, if the amine reactant is a diamino compound, for example, ethylenediamine, the number of moles would be one half, i.e., the equivalent ratio.

The monohydric hydroxyl-containing organic compounds will generally be used in at least an equimolar amount with the amine reactant, with the mole ratio of monohydric hydroxyl-compound to amine reactant preferably being from at least 2:1 to about 20:1, and most preferably from about 6:1 to 12:1. The amount of polyhydric alcohol which will be generally employed as the hydroxyl-containing organic compound can be determined from the foregoing mole ratios of monohydric alcohol to amine reactant and will, of course, be based on the number of reactive hydroxyl groups in each molecule of the alcohol, e.g., at least 0.5 mole of ethylene glycol will generally be used for each mole of amine reactant in the preparation of the corresponding N-phenyl carbamate derivative of ethylene glycol.

The amount of solvent is also not critical and, where used, will generally range from about 1 to 50 weight percent, and preferably from about 10 to 40 weight percent, of the reaction mixture.

The order of mixing the reactants is not critical and can be varied within the limitations of the equipment employed. A simple procedure is to charge the amine reactant, the organic compound containing at least one hydroxyl group, and the metal reactant into the reaction vessel, introduce the proper amount of the source of carbon monoxide and then heat the mixture to obtain the desired reaction. A suitable pressure vessel, such as an autoclave, which is preferably provided with heating means and agitation means, such as a stirrer or an external rocking mechanism, is employed for the reaction.

Generally, the amount of gaseous carbon monoxide in the free space of the reactor is sufficient to maintain the desired pressure as well as to provide a reactant for the process. As the reaction progresses an additional source of carbon monoxide can be fed to the reactor either intermittently or continuously. Although greater and lesser amounts of the source of carbon monoxide can be employed if desired, generally the total amount of the source of carbon monoxide added during the reaction is between about 3 and about 50 moles and preferably between about 8 and about 15 moles of CO per non-cyclic group containing the active amine group of the amine reactant nitrogen atom. The highest carbon monoxide requirements are generally utilized in a process in which carbon monoxide gas is added continuously, but suitable recycle of carbon monoxide containing gas streams greatly reduces the overall consumption of carbon monoxide.

The reaction temperature is generally maintained in the range of from about 60° to about 250° and preferably from about 100° to 200° C., and more preferably from about 150° to 180° C. These temperature ranges permit a convenient rate of reaction to be achieved while avoiding undesirable side reactions. It will be understood, however, that any elevated temperatures below that at which the starting materials or the products decompose can be used. The reaction is carried out, as indicated above, at superatmospheric pressures which is normally between about 10 and about 500 atmospheres, although higher or lower reaction pressures can be employed if other reaction conditions are suitably adjusted. Preferably, however, only moderate carbon monxide pressures in the range of about 10 to about 100 atmospheres are employed and the reaction is conveniently run at a temperature of below about 200° C. within this pressure range.

The process of the present invention can be carried out batchwise, semi-continuously or even continuously. The reaction time is dependent upon the nature of the reactants, temperature, pressure and the type of metal reactant employed, as well as the type of equipment which is used. The process of this invention can be carried out in a vapor phase or a liquid phase, or partially in vapor and liquid phases in the reaction zone.

After the reaction has been completed in the batchwise practice of this invention, the temperature of the reaction mixture can be dropped to ambient temperature and the pressure vessel vented. The reaction product is then treated by conventional procedures, including filtration, distillation, or other suitable separation techniques, to effect separation of urethane from unreacted starting material, solvent, by-product, reduced metal reactant, etc. Urea by-products, if any, can be readily recovered and recycled to the reaction zone, if desired, to suppress formation of the urea by-product therein.

The reduced metal reactant can also be readily recovered and treated for regeneration of the metal reactant. Such means of oxidizing the reduced metal reactant to the higher valence of state of the metal are conventional and their description is not necessary to an understanding of the process of this invention.

As indicated above, the amount of reaction by-products (e.g., formanilide and ureas when N-phenyl carbamates are the desired product) which are formed in the process of this invention is surprisingly low. While the amount of such N-containing by-products will vary, they will preferably be formed in a selectivity of less than 20 mole percent, more preferably less than 10 mole percent, and most preferably less than 5 mole percent, based on the amount of the metal reactant reacted.

The process of this invention, therefore, preferably forms the desired carbamate product in a selectivity of at least 80 mole percent, more preferably at least 90 mole percent, and most preferably at least 95 mole percent, based on the moles of the metal reactant reacted.

The urethane products obtained by the invention contain one or more urethane groups and can be monomeric or polymeric in nature. Thus, the process of the invention can be adapted for the preparation of monourethanes from monoamine compounds and monohydroxy compounds and adapted for the preparation of polyurethanes from polyamine compounds and monofunctional hydroxy compounds. The resulting urethane products, in particular those urethanes containing not more than three urethane groups per molecule, can be converted to corresponding isocyanates by suitable means, including thermal and catalytic means.

The process of this invention can be further illustrated by the following examples wherein parts are by weight unless otherwise indicated. In the Examples, analysis of gas and liquid samples is performed by gas chromotography, with toluene being used in the liquid samples as internal standard. Carbamate selectivities in the Examples are based on the moles of metal reactant reacted.

EXAMPLE 1

To a 200 cc Parr reactor provided with a glass liner (actual reactor volume with liner=134 cc) and a magnetic stirrer is charged, at room temperature, 20 mmoles aniline, 240 mmoles methanol and 6 mmoles of $PdCl_2$ as the metal reactant. The reactor is sealed and then purged with gaseous nitrogen by means of a gas inlet tube and, also at room temperature, CO is pressurized into the reactor, to provide a pressure in the reactor of about 1000 psig. The pressured reactor is then heated with stirring by means of an oil bath to 120° C., which is measured externally to the reactor. This reaction temperature is maintained for 24 hours, after which the oil bath is cooled to about 30° C. by passing cooling water through a copper tube which is immersed in the bath. The gas in the reactor is then vented and the vent gas and the liquid product mixture in the reactor are analyzed for methyl-N-phenyl carbamate which is found to be present in a selectivity of about 90%, based on the metal reactant charged.

EXAMPLE 2

The procedure of Example 1 is repeated except that 200 mmoles of isopropanol are used instead of methanol and the metal reactant comprises 3 mmoles of $CoCl_2$. After 24 hours of reaction at 120° C. employing a CO pressure of 1000 psig, selectivity to the methyl-N-phenyl carbamate is found to be about 87%.

EXAMPLE 3

Following the procedure of Example 1, 10 mmoles of 2,4-diamino toluene, 160 mmoles n-butanol and 4 mmoles of $Co(NO_3)_2$ as the metal reactant are charged to the reactor. After 24 hours of reaction at 120° C. employing a CO pressure of 1000 psig, selectivity to the mono- and bis-n-butyl carbamate, e.g.,

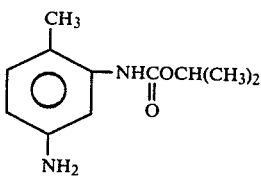

is found to be about 85%.

EXAMPLE 4

The procedure of Example 3 is repeated except that the metal reactant comprises 4 mmoles of $PdCl_2$. After 24 hours of reaction at 120°, employing a CO pressure of 1000 psig, selectivity to the mono- and bis-n-butyl carbamate is found to be about 81%.

EXAMPLE 5

Following the procedure of Example 1, the reactor is charged with 10 mmoles of 4,4'-methylenedianiline, 60 mmoles ethylene glycol and 2 mmoles of $PdBr_2$ as the metal reactant. After 24 hours of reaction at 120° C. employing a CO pressure of 1000 psig, selectivity to the mono- and bis-methyl carbamate, e.g.,

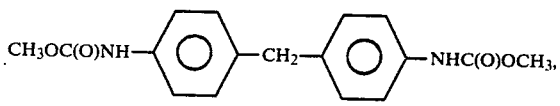

is found to be about 80%.

The above run is repeated except that 4 mmoles of $RhCl_3$ are employed as the metal reactant and similar results are obtained.

EXAMPLE 6

The procedure of Example 5 is repeated except that 170 mmoles of ethanol are used instead of ethylene glycol and 5 mmoles of $CoBr_2$ are used as the metal reactant. After 24 hours of reaction at 120° C. and CO pressure of 1000 psig, essentially no difference is noted in the formation of the corresponding mono- and bis-carbamate, e.g.,

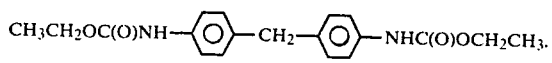

EXAMPLE 7

Following the procedure of Example 1, the reactor charged with 10 mmoles of $H_2N(CH_2)_6NH_2$, 15 mmoles of n-propanol and 12 mmoles of a 50:50 mole mixture of $Pd(O_2CCH_3)_2$ and $Fe(O_2CCH_3)_3$ as the metal reactants. Following 24 hours of reaction at 120° C. and a CO pressure of 1000 psig, selectivity to the corresponding mono- and bis-carbamate, e.g., $CH_3OC(O)NH(CH_2)_6NHC(O)OCH_3$, is found to be about 88%.

EXAMPLE 8

The procedure of Example 7 is repeated except that 80 mmoles of glycerol are used instead of n-propanol and 4 mmoles of $CoI_2$ are used as the metal reactant. Again, after 24 hours of reaction at 120° using a CO pressure of 1000 psig, selectivity to the mono-carbamate, $CH_2(OH)CH(OH)CH_2OC(O)NH(CH_2)_6NHOC(O)CH_2CH(OH)CH_2OH$ is found to be about 82%.

EXAMPLE 9

The procedure of Example 1 is repeated except that 20 mmoles ortho-toluidiene are used instead of aniline, and essentially no difference in results is noted in the formation of methyl-N-ortho-tolyl carbamate.

EXAMPLE 10

The procedure of Example 1 is repeated except that 20 mmoles cyclohexylamine are used instead of aniline, and essentially no difference in results is noted in the formation of methyl-N-cyclohexyl carbamate.

EXAMPLE 11

The procedure of Example 1 is repeated except that the alcohol reactant comprises, in separate runs, cyclohexanol, benzyl alcohol and butyl alcohol, respectively, and essentially no difference is noted in the formation of cyclohexyl-N-phenyl carbamate, benzyl-N-phenyl carbamate and butyl-N-phenyl carbamate, respectively.

EXAMPLE 12

The procedure of Example 1 is repeated except that 20 mmoles of N-butyl amine are used instead of aniline, and essentially no difference in results is noted in the formation of methyl-N-butyl carbamate.

It will be obvious that various changes and modifications can be made without departing from the invention, and it is intended, therefore, that all matter contained in the foregoing description shall be interpreted as illustrative only and not as limitative of the invention.

I claim:

1. A process for producing carbamates which comprises contacting a reactant consisting essentially of an organic primary or secondary amine selected from the group consisting of aliphatic amines, alicyclic amines and aromatic amines having the formula
   (i) $RNH_2$,
   (ii) $RNH(R')$, or
   (iii) $R(NH_2)_m$ wherein R and R' are independently selected from a group consisting of alkyl, aryl, alkaryl, arakyl, and cycloalkyl and wherein m is an integer of from 2 to 5, and substituted derivatives of the foregoing groups wherein the substituent is inert and is a member selected from the group consisting of alkyl, aryl, alkaryl, aralkyl, cycloalkyl, halogen, cyano, tertiary amino, carboxyl, ether and thioether, and amino-substituted derivatives of the foregoing hydrocarbon substituents to the R and R' groups, in a reaction zone at a temperature of from about 60° to 250° C. under substantially anhydrous conditions and in the substantial absence of reactive oxygen with (1) carbon monoxide, (2) an organic compound which contains at least one hydroxyl group per molecule and which is selected from the group consisting of compounds of the formula $Z(OH)_n$ wherein n is an integer of at least one and Z is an optionally substituted aliphatic, cycloaliphatic or araliphatic group, and (3) a metal reactant consisting essentially of a non-carbonyl compound or complex of a metal of Group VIII of the Periodic Table to form the carbamate corresponding to said amine and said hydroxyl-containing organic compound, said metal being in at least a +2 valence state in said metal reactant, said metal reactant being employed in a molar ratio of the moles of metal in the metal reactant to the moles of amine reactant charged of from about 0.05:1 to 5:1.

2. The process according to claim 1 wherein the metal reactant consists essentially of an inorganic salt of a Group VIII metal.

3. The process according to claim 1 wherein the metal reactant consists essentially of an inorganic compound of a Group VIII metal.

4. The process according to claim 1 wherein the amine reactant is an aromatic primary amine of from 6 to 24 carbon atoms.

5. The process according to claim 4 wherein the amine reactant comprises at least one member selected from the group consisting of aniline and alkyl-substituted anilines of up to 12 carbon atoms.

6. The process according to claim 1 wherein the hydroxyl group-containing compound comprises at least one member selected from the group consisting of monohydric alcohols having from 1 to 20 carbon atoms.

7. The process according to claim 1 wherein the hydroxyl group-containing compound comprises at least one member selected from the group consisting of polyhydric compounds containing up to 20 carbon atoms.

8. The process according to claim 1 wherein the hydroxyl group-containing compound comprises a lower alkanol having from 1 to 10 carbon atoms.

9. The process according to claim 1 wherein the reaction zone additionally contains a liquid organic base.

10. The process according to claim 1 wherein the metal reactant consists essentially of an oxide, hydroxide, sulfide, silicate, sulfate, phosphate, arsenate, nitrate, carbonate, halide or acetate of a metal selected from the group consisting of Fe, Ru, Os, Co, Rh, Ir, Ni, Pd and Pt, and mixtures thereof.

11. The process according to claim 10, wherein the metal consists essentially of Co or Pd.

12. A process for producing carbamates which comprises contacting an amine selected from the group consisting of aromatic primary mono- and di-amines of from 6 to 14 carbon atoms in a reaction zone at a temperature of from about 100° to 200° C. and a carbon monoxide pressure of from 10 to 100 atmospheres, under substantially anhydrous conditions and in the substantial absence of molecular oxygen with carbon monoxide, a hydroxyl group-containing compound selected from a group consisting of mono- and polyhydric alcohols of up to 7 carbon atoms and a metal reactant consisting essentially of a non-carbonyl compound or complex of a metal of Group VIII of the Periodic Table to form the carbamate corresponding to said amine and said hydroxyl-containing organic compound, said metal reactant being employed in an amount sufficient to provide from about 0.05 to 5 moles of said metal per mole of said amine reactant charged, said metal being in at least a +2 valence state in said metal reactant.

13. The process according to claim 12 wherein the reaction zone additionally contains an organic solvent is selected from the group consisting of pyridine and dialkyl-amino pyridines.

14. The process according to claim 12 wherein the metal reactant comprises a compound or complex of palladium or cobalt.

* * * * *

UNITED STATES PATENT AND TRADEMARK OFFICE
CERTIFICATE OF CORRECTION

PATENT NO. : 4,260,781
DATED : April 7, 1981
INVENTOR(S) : Robert J. Harvey

It is certified that error appears in the above-identified patent and that said Letters Patent are hereby corrected as shown below:

Col. 1, line 10 - "May 9, 1979" should be --May 25, 1979--
Col. 2, line 15 - "596-572" should be --569-572--
Col. 3, line 30 - "carbmate" should be --carbamate--
Col. 6, line 30 - "changed" should be --charged--
Col. 7, line  7 - "p-propanol" should be --n-propanol--
Col. 7, line 37 - "N, N'-dimethyl" should be --N, N-dimethyl--
Col. 8, line 36 - "congaining" should be --containing--
Col. 9, line 53 - "monxide" should be --monoxide--
Col. 10, line 46 - "chromotography" should be --chromatography--
Col. 12, line  3 - add "is" to the end of the line
Col. 12, line  4 - "15" should be --150--

Signed and Sealed this

Thirtieth Day of March 1982

[SEAL]

Attest:

GERALD J. MOSSINGHOFF

Attesting Officer  Commissioner of Patents and Trademarks